(12) United States Patent
Riehl

(10) Patent No.: US 7,857,746 B2
(45) Date of Patent: Dec. 28, 2010

(54) SYSTEM AND METHOD TO REDUCE DISCOMFORT USING NERVE STIMULATION

(75) Inventor: Mark Edward Riehl, Doylestown, PA (US)

(73) Assignee: Nueronetics, Inc., Malvern, PA (US)

(*) Notice: Subject to any disclaimer, the term of this patent is extended or adjusted under 35 U.S.C. 154(b) by 1635 days.

(21) Appl. No.: 10/977,734

(22) Filed: Oct. 29, 2004

(65) Prior Publication Data

US 2006/0094924 A1 May 4, 2006

(51) Int. Cl.
*A61N 1/00* (2006.01)

(52) U.S. Cl. .......................................... 600/13

(58) Field of Classification Search ............... 600/9–15; 607/63–66, 72, 69, 100–103, 108–110
See application file for complete search history.

(56) References Cited

U.S. PATENT DOCUMENTS

| | | | |
|---|---|---|---|
| 3,658,051 | A | 4/1972 | Maclean |
| 3,683,923 | A | 8/1972 | Anderson |
| 4,473,074 | A | 9/1984 | Vassiliadis |
| 4,601,753 | A | 7/1986 | Soileau et al. |
| 4,638,798 | A | 1/1987 | Shelden et al. |
| 4,712,558 | A | 12/1987 | Kidd et al. |
| 4,940,453 | A | 7/1990 | Cadwell |
| 4,994,015 | A | 2/1991 | Cadwell ................. 600/13 |
| 4,995,395 | A | 2/1991 | Ilmoniemi et al. |
| 5,047,005 | A | 9/1991 | Cadwell |
| 5,061,234 | A | 10/1991 | Chaney |
| 5,078,674 | A | 1/1992 | Cadwell ................. 600/13 |
| 5,097,833 | A | 3/1992 | Campos |
| 5,116,304 | A | 5/1992 | Cadwell ................. 600/13 |
| 5,154,723 | A | 10/1992 | Kubota et al. |
| 5,254,123 | A | 10/1993 | Bushey |

(Continued)

FOREIGN PATENT DOCUMENTS

EP 1 273 320 A1 1/2003

(Continued)

OTHER PUBLICATIONS

Baudewig, J. et al., "Functional MRI of Cortical Activations Induced by Transcranial Magnetic Stimulation(TMS)", *Brain Imaging-NeuroReport*, 2001, 12(16), 3543-3548.

(Continued)

*Primary Examiner*—Charles A Marmor, II
*Assistant Examiner*—Christine D Hopkins
(74) *Attorney, Agent, or Firm*—Woodcock Washburn LLP

(57) ABSTRACT

A novel method and system for performing transcutaneous magnetic stimulation is disclosed herein. In the method, a first magnetic field is generated using a first magnetic stimulation device for transcutaneously stimulating a treatment area, and a second magnetic field for transcutaneously stimulating the treatment area is generated by a second magnetic stimulation device. In addition, a novel method and system for reducing discomfort caused by transcutaneous magnetic stimulation is disclosed herein. In the method, a first magnetic field is created at a first and second location using a first magnetic stimulation device. The first magnetic field causes magnetic stimulation at the first and second locations. A second magnetic field is created at the second location using a second magnetic stimulation device, thereby reducing stimulation at the second location.

32 Claims, 11 Drawing Sheets

U.S. PATENT DOCUMENTS

| | | | |
|---|---|---|---|
| 5,299,569 A | 4/1994 | Wernicke et al. | |
| 5,566,681 A | 10/1996 | Manwaring et al. | |
| 5,707,334 A | 1/1998 | Young | 600/9 |
| 5,725,471 A | 3/1998 | Davey et al. | |
| 5,766,124 A | 6/1998 | Polson | |
| 5,769,778 A | 6/1998 | Abrams et al. | |
| 5,812,301 A | 9/1998 | Nakamura et al. | |
| 5,813,970 A | 9/1998 | Abrams et al. | |
| 5,820,623 A | 10/1998 | Ng | |
| 6,057,373 A | 5/2000 | Fogel | |
| 6,066,084 A | 5/2000 | Edrich et al. | |
| 6,074,385 A | 6/2000 | Klopotek | |
| 6,086,525 A | 7/2000 | Davey et al. | |
| 6,117,066 A | 9/2000 | Abrams et al. | |
| 6,132,361 A * | 10/2000 | Epstein et al. | 600/13 |
| 6,155,966 A | 12/2000 | Parker | |
| 6,169,963 B1 | 1/2001 | Markov | |
| 6,179,769 B1 | 1/2001 | Ishikawa et al. | 600/9 |
| 6,179,770 B1 | 1/2001 | Mould | |
| 6,179,771 B1 | 1/2001 | Mueller | 600/13 |
| 6,198,958 B1 | 3/2001 | Ives et al. | 600/411 |
| 6,205,356 B1 | 3/2001 | Holcomb | |
| 6,210,317 B1 | 4/2001 | Bonlie et al. | |
| 6,253,109 B1 | 6/2001 | Gielen | |
| 6,256,531 B1 | 7/2001 | Ilmoniemi et al. | 600/544 |
| 6,266,556 B1 | 7/2001 | Ives et al. | |
| 6,279,579 B1 | 8/2001 | Riaziat et al. | |
| 6,355,049 B1 | 3/2002 | Gill | |
| 6,366,814 B1 | 4/2002 | Boveja et al. | |
| 6,389,318 B1 | 5/2002 | Zarinetchi et al. | |
| 6,402,678 B1 | 6/2002 | Fischell et al. | 600/13 |
| 6,413,263 B1 | 7/2002 | Lobdill et al. | |
| 6,425,852 B1 | 7/2002 | Epstein et al. | |
| 6,463,328 B1 | 10/2002 | John | 607/45 |
| 6,477,410 B1 | 11/2002 | Henley et al. | |
| 6,480,743 B1 | 11/2002 | Kirkpatrick et al. | |
| 6,484,059 B2 | 11/2002 | Gielen | 607/45 |
| 6,488,617 B1 | 12/2002 | Katz | |
| 6,497,648 B1 | 12/2002 | Rey | |
| 6,503,187 B1 | 1/2003 | Ilmoniemi et al. | 600/14 |
| 6,516,288 B2 | 2/2003 | Bagne | 702/179 |
| 6,537,197 B1 | 3/2003 | Ruohonen et al. | |
| 6,551,233 B2 | 4/2003 | Perreault et al. | |
| 6,560,490 B2 | 5/2003 | Grill et al. | 607/72 |
| 6,567,702 B1 | 5/2003 | Nekhendzy et al. | |
| 6,571,123 B2 | 5/2003 | Ives et al. | 600/544 |
| 6,572,528 B2 | 6/2003 | Rohan et al. | |
| 6,591,138 B1 | 7/2003 | Fischell et al. | |
| 6,618,614 B1 | 9/2003 | Chance | |
| 6,629,935 B1 | 10/2003 | Miller et al. | |
| 6,641,520 B2 | 11/2003 | Bailey et al. | |
| 6,663,556 B2 | 12/2003 | Barker | 600/14 |
| 6,827,681 B2 | 12/2004 | Tanner et al. | |
| 6,849,040 B2 | 2/2005 | Ruohonen et al. | |
| 6,978,179 B1 | 12/2005 | Flagg et al. | |
| 7,367,936 B2 | 5/2008 | Myers et al. | |
| 7,407,478 B2 | 8/2008 | Zangen et al. | |
| 2001/0018547 A1 | 8/2001 | Mechlenburg et al. | |
| 2001/0031906 A1 | 10/2001 | Ishikawa et al. | 600/13 |
| 2002/0013612 A1 | 1/2002 | Whitehurst | |
| 2002/0087201 A1 | 7/2002 | Firlik et al. | 607/45 |
| 2002/0091419 A1 | 7/2002 | Firlik et al. | 607/45 |
| 2002/0103515 A1 | 8/2002 | Davey et al. | 607/66 |
| 2002/0123780 A1 | 9/2002 | Grill et al. | |
| 2002/0160436 A1 | 10/2002 | Markov et al. | |
| 2002/0169355 A1 | 11/2002 | Rohan et al. | |
| 2003/0004392 A1 | 1/2003 | Tanner et al. | 600/9 |
| 2003/0023159 A1 | 1/2003 | Tanner | 600/417 |
| 2003/0028072 A1 | 2/2003 | Fischell et al. | 600/13 |
| 2003/0050527 A1 | 3/2003 | Fox et al. | 600/13 |
| 2003/0073899 A1 | 4/2003 | Ruohonen et al. | 600/417 |
| 2003/0074032 A1 | 4/2003 | Gliner et al. | |
| 2003/0082507 A1 | 5/2003 | Stypulkowski | |
| 2003/0087264 A1 | 5/2003 | Kaplitt et al. | |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2003/0195588 A1 | 10/2003 | Fischell et al. | 670/55 |
| 2003/0204135 A1 | 10/2003 | Bystritsky | 600/407 |
| 2004/0010177 A1 | 1/2004 | Rohan et al. | 600/9 |
| 2004/0051279 A1 | 3/2004 | Grant et al. | |
| 2004/0077921 A1 | 4/2004 | Becker et al. | |
| 2004/0077923 A1 | 4/2004 | Frimerman et al. | |
| 2004/0122281 A1 | 6/2004 | Fischell et al. | |
| 2004/0127942 A1 | 7/2004 | Yomtov et al. | |
| 2004/0138524 A1 | 7/2004 | Ueda et al. | |
| 2004/0138550 A1 | 7/2004 | Hartlep et al. | |
| 2004/0143300 A1 | 7/2004 | Rogers | |
| 2004/0153129 A1 | 8/2004 | Pless et al. | |
| 2004/0172012 A1 | 9/2004 | Otsuka et al. | |
| 2004/0193001 A1 | 9/2004 | Miller | |
| 2004/0204625 A1 | 10/2004 | Riehl et al. | |
| 2005/0021104 A1 | 1/2005 | DiLorenzo | |
| 2005/0124848 A1 | 6/2005 | Holzner | |
| 2005/0216071 A1 | 9/2005 | Devlin et al. | |
| 2005/0228209 A1 | 10/2005 | Schneider et al. | |
| 2005/0256539 A1 | 11/2005 | George et al. | |
| 2006/0199992 A1 * | 9/2006 | Eisenberg et al. | 600/14 |

FOREIGN PATENT DOCUMENTS

| | | |
|---|---|---|
| WO | WO 99/64884 | 12/1999 |
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 03/039468 A2 | 5/2003 |
| WO | WO 03/082405 A1 | 10/2003 |
| WO | WO 03/084605 A1 | 10/2003 |
| WO | WO 03/085546 A1 | 10/2003 |
| WO | WO 03/090604 A2 | 11/2003 |
| WO | WO 03/098268 A1 | 11/2003 |
| WO | WO 2004/006750 A2 | 1/2004 |
| WO | WO 2004/082759 A2 | 9/2004 |
| WO | WO 2004/100765 A2 | 11/2004 |
| WO | WO 2005/000401 A1 | 1/2005 |
| WO | WO 2005/065768 A1 | 7/2005 |

OTHER PUBLICATIONS

Bohning, D.E. et al., "A TMS Coil Positioning/Holding System for MR Image-Guided TMS Interleaved with fMRI", *Clinical Neurophysiology*, 2003, 114, 2210-2219.

Bohning, D.E. Ph.D. et al., "A Combined TMS/fMRI Study of Intensity-Dependant TMS over Motor Cortex", *Society of Biological Psychiatry*, 1999, 45, 385-394.

Bohning, D.E. Ph.D. et al., "Bold-fMRI Response to Single-Pulse Transcranial Magnetic Stimulation (TMS)", *Journal of Magnetic Resonance Imaging*, 2000, 11, 569-574.

George, M.S. et al., "A Controlled Trial of Daily Left Prefrontal Cortex TMS for Treating Depression", *Society of Biological Psychiatry*, 2000, 48, 962-970.

Grafman, J. Ph.D., "TMS as a Primary Brain Mapping Tool" *Transcranial Magnetic Stimulation in Neuropsychiatry*, 2000, 115-140.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lorberbaum, J.P., M.D. et al., "Safety Concerns of TMS", *Transcranial Magnetic Stimulation in Neuropsychiatry*, 2000, 141-161.

Loo, C.K. et al., "Transcranial Magnetic Stimulation (TMS) in Controlled Treatment Studies: Are Some "Sham" Forms Active?", *Society of Biological Psychiatry*, 2000, 47, 325-331.

Nahas, Z. et al., "Unilateral Left Prefrontal Transcranial Magnetic Stimulation(TMS) Produces Intensity-Dependent Bilateral Effects as Measured by Interleaved BOLD fMRI", *Society of Biological Psychiatry*, 2001, 50, 712-720.

Nahas, Z. et al., "Left Prefrontal Transcranial Magnetic Stimulation(TMS) Treatment of Depression in Bipolar Affective Disorder: A Pilot Study of Acute Safety and Efficacy", *BiPolar Disorders*, 2003, 5, 40-47.

Pridmore, S., "Substitution of Rapid Transcranial Magnetic Stimulation Treatments for Electroconvulsive Therapy Treatments in a Course of Electroconvulsive Therapy", *Depression and Anxiety*, 2000, 12, 118-123.

Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.

Awiszus, F. et al., "Characterization of Paired-Pulse Transcranial Magnetic Stimulation Conditions Yielding Intracortical Inhibition of I-Wave Facilitation using a Threshold Paradigm", *Experimental Brain Research*, 1999, 129, 317-324.

Garcia-Toro, M. et al., "Modest Adjunctive Benefit with Transcranial Magnetic Stimulation in Medication-Resistant Depression", *Journal of Affective Disorders*, 2001, 64, 271-275.

George, M.S. "New Methods of Minimally Invasive Brain Modulation as Therapies in Psychiatry: TMS,MST,VNS and DBS", *Chinese Medical Journal (Taipei)*, 2002, 65, 349-360.

Hess, C.W. et al., "Magnetic Stimulation of the Human Brain: Influence of Size and Shape of the Stimulating Coil", *Motor Disturbances II*, 1990, 3, 31-42.

Keiji, I. et al., "Effects of Transcranial Magnetic Stimulation on EEG Activity", *IEEE transactions on Magnetics*, 2002, 38(5), 3347-3349, XP 011075410.

Lisanby, S.H. et al., "Sham TMS: Intracerebral Measurement of the Induced Electrical Field and the Induction of Motor-Evoked Potentials", *Society of Biological Psychiatr*, 2001, 49, 460-463.

Lisanby, S.H. MD. et al., "Magnetic Seizure Therapy of Major Depression", *Arch Gen Psychiatry*, 2001, 58, 303-307.

Lisanby, S.H., "Safety and Feasibility of Magnetic Seizure Therapy(MST) in Major Depression: Randomized Within-Subject Comparasion with Electroconvulsive Therapy", *Neuropsychopharmacology, New York State Psychiatric Institute*, 2003, 28, 1852-1865.

Pascual-Leone, A. et al., "Rapid-Rate Transcranial Magnetic Stimulation of Left Dorsolateral Prefrontal Cortex in Drug-Resistant Depression", *The Lancet*, 1996, 18, 233-237.

Pridmore, S., "Rapid Transcranial Magnetic Stimulation and Normalization of the Dexamethasone Suppression Test", *Psychiatry and Clinical Neurosciences*, 1999, 53, 33-37.

Roth, Y. et al., "A Coil Design for Transcranial Magnetic Stimulation of Deep Brain Regions", *Journal of Clinical Neurophysiology*, 2002, 19(4), 361-370.

Sommer, M. et al., "Increased Transcranial Magnetic Motor Threshold after ECT", *European Archives of Psychiatry and Clinical Neuroscience*, 2002, 252, 250-252.

Terrace, H.S. et al., "The Cognitive Effects of Electroconvulsive Shock and Magnetic Seizure Therapy in Rhesus Monkeys", *Society for Neuroscience Abstract Viewer and Itinerary Planner*, 2002, Abstract Only # 184.14.

Terrace, H.S. et al., "The Cognitive Effects of Electroconvulsive Shock Stimulation and Magnetic Seizure Therapy in Rhesus Monkeys", *Society for Neuroscience Abstracts*, 2001, 27(1), 536.7, p. 1418.

Trivedi, M.H., MD., "Treatment-Resistant Depression: New Therapies on the Horizon", *Annals of Clinical Psychiatry*, 2003, 15(1), 59-70.

Wassermann, E.M., "Repetitive Transcranial Magnetic Stimulation: An Introduction and Overview", *CNS Spectrums, The International Journal of Neuropsychiatric Medicine*, Jan. 1997, 7 pages.

* cited by examiner

SYSTEM AND METHOD TO REDUCE DISCOMFORT USING NERVE STIMULATION

FIELD OF THE INVENTION

The invention relates to the field of transcutaneous stimulation. Specifically, the invention relates to using magnetic fields to reduce discomfort.

BACKGROUND OF THE INVENTION

A number of medical ailments are treated or treatable through the application of electrical stimulation to an afflicted portion of a patient's body. Neurons, muscle and tissue cells are all forms of biological tissue capable of carrying electrical signals and responding to electrical stimuli. Two examples of electrical stimulation may include magnetic or inductive stimulation which may make use of a changing magnetic field, and electric or capacitive stimulation in which an electric field may be applied to the tissue.

For example, when an electrical conductor is passed through a magnetic field, an electric field is induced causing current to flow in the conductor. Because various parts of the body are also conductive, when a changing magnetic field is applied to the portion of the body, an electric field is created in the conductive tissue, thereby causing current to flow. In the context of biological tissue, for example, the resultant flow of electric current can stimulate the tissue by causing neurons in the tissue to depolarize. Also, in the context of muscles, for example, muscles associated with the stimulated neurons contract.

Electrical stimulation has many beneficial and therapeutic biological effects. For example, magnetic stimulation is effective in rehabilitating injured or paralyzed muscle groups. Magnetic stimulation is also proving effective for treatment of the spine, which is difficult to access directly because vertebrae surround it. Magnetic stimulation may be used to block the transmission of pain via nerves in the back (e.g., the nerves responsible for lower back pain) or via other nerves in other locations. Further, and unlike the other medical processes that stimulate the body, magnetic field stimulation may be non-invasive. For example, using magnetic fields to generate current in the body produces stimulation by passing the magnetic field through the skin of a patient. In contrast, conventional electric stimulation pain treatment methods for lower back pain involve the placement of electrodes in the spinal cord to enable stimulation. For peripheral nerves, a needle may be inserted proximate the problematic nerve to enable electric stimulation.

Magnetic stimulation also has proven effective in stimulating regions of the brain. One area of particular therapeutic interest is the treatment of neuropsychiatric disorders. It is believed that more than 28 million people in the United States alone suffer from some type of neuropsychiatric disorder. These include specific conditions such as depression, schizophrenia, mania, obsessive-compulsive disorder, panic disorders, just to name a few. One particular condition, depression, is believed to affect 19 million people in the United States alone, and possibly 340 million people worldwide. Modern medicine offers depression patients a number of treatment options, including several classes of anti-depressant medications such as selective serotonin reuptake inhibitors (SSRIs), MAIs, tricyclics, lithium, and electroconvulsive therapy (ECT). Yet many patients remain without satisfactory relief from the symptoms of depression. To date, ECT remains an effective treatment for major depressive disorder; however, many patients will not undergo the procedure because of its severe side effects.

Recently, repetitive transcranial magnetic stimulation (rTMS) has been shown to have significant anti-depressant effects for patients, even those that do not respond to the traditional methods and medications. In one embodiment of rTMS, a subconvulsive stimulation is applied to the prefrontal cortex in a repetitive manner, causing a depolarization of cortical neurons. The neurons are depolarized by the induction of an electric field, usually in excess of one volt per centimeter (V/cm). These electric fields result from a rapidly changing magnetic field applied non-invasively.

It is now well known to those skilled in the art that both the left and right prefrontal cortex regions of the brain have strong communication links to Limbic System structures, which contain the "circuits" controlling mood and general behavior. One objective of rTMS is to provide stimulation to these biological circuits through a non-invasive, sub-convulsive technique to relieve the symptoms of depression without many of the negative side effects of ECT or medications. However, one reported side effect of rTMS for the treatment of depression is patient discomfort at the site of the stimulation. It should be appreciated that discomfort may also be present in other forms of magnetic stimulation to other areas of the body. In the case of rTMS, this discomfort is caused, in part, by the depolarization of neuron membranes in the scalp and the resulting scalp muscle contractions that occur at the frequency of the rTMS. Testing has shown that approximately 20% of rTMS patients report this discomfort to be at a level that is very uncomfortable. In general, the greater the power and the higher the frequency of the therapeutic magnetic stimulation, the more discomfort is reported. Yet, reducing the power levels may not be a viable option because greater power has been shown to desirably stimulate deeper structures. Also, relatively higher frequencies (e.g., greater than 1 Hertz (Hz)) have been shown to have a greater anti-depressant effect.

Other types of discomfort may be caused by any number of ailments, and not exclusively as a side effect of rTMS. In addition, a patient may experience discomfort at locations other than the head area, such as at peripheral nerves and the like. Such locations may be at any location and at any depth within a patient's body. In such cases, it would be advantageous to reduce discomfort regardless of where the discomfort-causing nerve is located. Accordingly, it is desirable to develop techniques for reducing discomfort, whether caused by electrical stimulation or by other causes. In addition, it is desirable to develop techniques to more accurately stimulate a desired region of a patient while minimizing stimulation of surrounding tissue.

SUMMARY OF THE INVENTION

The invention is directed to a novel method and system for performing transcutaneous magnetic stimulation. In particular, the invention is directed to a novel method and system for using two or more magnetic stimulation devices for producing a focused magnetic field at a treatment area. In addition, the invention is directed to a novel method and system for reducing discomfort using two or more independently-driven magnetic stimulation devices.

DETAILED DESCRIPTION OF ILLUSTRATIVE EMBODIMENTS

Figure 1:
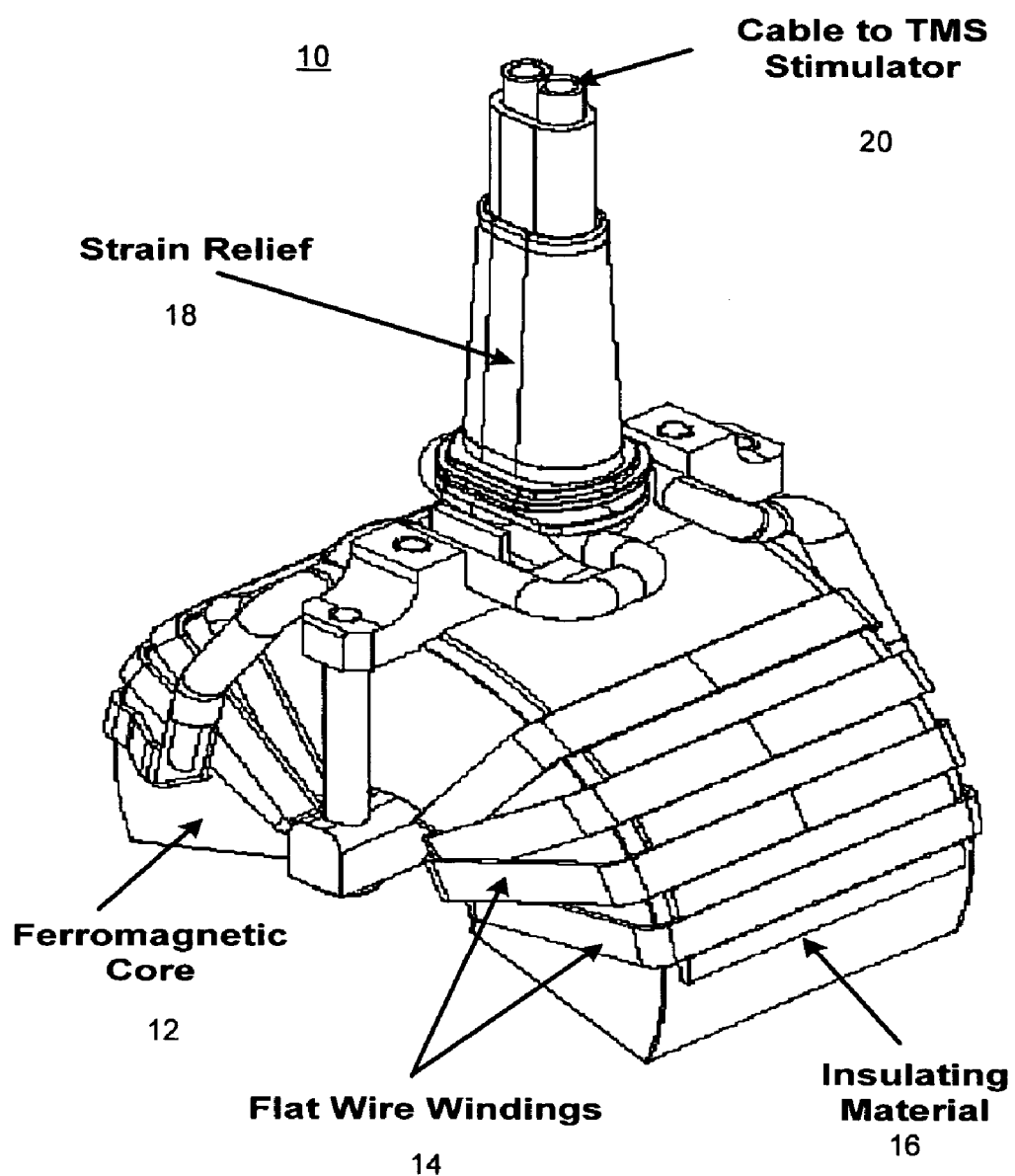
FIG. 1 is a diagram illustrating an exemplary ferromagnetic core material magnetic stimulation device that may be used in connection with an embodiment of the present invention.

The subject matter of the present invention is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Overview

In 1831, Michael Faraday discovered that the magnitude of an electric field induced on a conductor is proportional to the rate of change of magnetic flux density that cuts across the conductor. Faraday's law, well known to those skilled in the art, may be represented as $E \alpha -(dB/dt)$, where E is the induced electric field in Volts/meter, dB/dt is the time rate of change of magnetic flux density in Tesla/second. In other words, the amount of electric field induced in an object such as a conductor is determined by two factors: the magnetic flux density and the time rate of change of the flux density. The greater the flux density and its derivative, the greater the peak induced electric field and resulting peak current density. Because the magnetic flux density decreases in strength as the square of the distance from the source of the magnetic field, the flux density is greater the closer the conductor is to the source of the magnetic field. When the conductor is a coil, the current induced in the coil by the electric field may be increased in proportion to the number of turns of the coil and the area of the coil.

When an electric field is induced in a conductor, the electric field creates a corresponding current flow in the conductor. The current flow is in the same direction of the electric field vector at a given point. The peak electric field occurs when dB/dt is the greatest and diminishes at other times. If the electric field decreases, for example after a magnetic pulse, the current flows in a direction that tends to preserve the electric field (i.e., Lenz's Law).

In the context of electrical stimulation of the anatomy, certain parts of the anatomy (e.g., nerves, tissue, muscle, brain) act as a conductor and carry electric current when an electric field is presented. The electric field may be presented to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron action potential may be reduced to the extent that the membrane sodium channels open and an action potential response is created. An impulse of current is then propagated along the axon membrane that transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that depression is alleviated.

In a similar fashion, non-cortical neurons (e.g., cranial nerves, peripheral nerves, sensory nerves) may also be stimulated by an induced electric field. Techniques have been developed to intentionally stimulate peripheral nerves to diagnose neuropathologies by observing response times and conduction velocities in response to a pulsed magnetic field induced stimulus. Discomfort and/or pain may result if the induced electric field applied to a peripheral or cranial nerve is very intense or focused on a small area of such a nerve. This discomfort may be diminished by intentionally over-stimulating the sensory nerves in the affected nerve bundle so that they can no longer respond to external pain stimuli, or by reducing the intensity and focus of the induced electric field that is causing the pain sensation.

As noted above, it should be appreciated that transcutaneous magnetic stimulation is not limited to treatment of depression. In addition to depression, the transcutaneous magnetic stimulation methods and apparatus of the invention may be used to treat a patient such as a human suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and generalized anxiety disorder), post-traumatic stress disorder (one of the anxiety disorders in DSM), obsessive compulsive disorder (also one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, cannabis and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, and/or eating disorders (such as bulimia, anorexia and binge eating).

For purposes of explanation and clarity, the discussion herein focuses primarily on the treatment of discomfort caused by transcranial magnetic stimulation techniques as well as discomfort reduction in peripheral nerves. It will be appreciated that the invention is equally applicable to any type of discomfort, and can be used to treat nerves at any location within a patient's body. In addition, the invention may be employed in connection with any type of transcutaneous magnetic stimulation, and is in no way limited to transcranial applications.

Exemplary Ferromagnetic Core Stimulation Device

A ferromagnetic core may be used to produce a magnetic field for purposes of carrying out transcutaneous magnetic stimulation such as, for example, Transcranial Magnetic Stimulation (TMS), Repetitive TMS (rTMS), Magnetic Seizure Therapy (MST), reduction of peripheral nerve discomfort and so forth. Again, although the examples that follow are discussed in connection with TMS and rTMS embodiments for the purposes of explanation and clarity, any type of transcutaneous magnetic stimulation, including all of those listed above, may be performed according to an embodiment of the invention.

In addition, the invention is not limited to the use of ferromagnetic core magnetic stimulation devices, as other core materials may be used such as for example an air core magnetic stimulation device. The discussion herein describes a ferromagnetic core magnetic stimulation device for purposes of explanation and clarity. In one embodiment, a ferromagnetic core may be approximately hemispherical, and in another embodiment the ferromagnetic core may include a highly saturable magnetic material having a magnetic saturation of at least 0.5 Tesla. In some embodiments, a ferromagnetic core may be shaped to optimize the magnetic field distribution in the treatment area. Treatment areas for other forms of treatment (e.g., reduction of discomfort in peripheral nerves, etc.) may be more or less deep that is the case for TMS. The ferromagnetic core permits efficient localization of the generated magnetic field. Effectively targeting a treatment location can reduce discomfort by either appropriately treating a problematic nerve, or by treating a treatment area without also undesirably stimulating neighboring nerves.

A typical ferromagnetic core coil for TMS applications is designed to produce a magnetic field that exceeds the cortical stimulation threshold over a 2-3 cm region near the surface of the brain. It will be appreciated that the magnetic field further diminishes at points deeper in the cortex. A deeper anatomical structure (such as a cranial nerve passing through a foramen in the skull) that has a significantly higher conductivity than adjacent tissue will tend to concentrate any current induced by the pulsed magnetic field. This concentration effect can elevate the local current density above the neuron stimulation threshold in the focal areas of highest conductivity. If the structure is a sensory nerve (e.g., trigeminal bundle) it could be stimulated even though it is located outside the region where the magnetic field exceeds the cortical stimulation threshold. Conventional solutions to this problem include repositioning the TMS coil away from the affected nerve, re-orienting the magnetic field so that the vector of the induced current is not parallel with the affected nerve, or designing the TMS coil with smaller dimensions so that the field falls off faster with distance. It will be appreciated to one skilled in the art that these solutions may have adverse impacts on the intended therapy.

In contrast, an embodiment of the invention uses additional coils in conjunction with the TMS coil that are designed and placed in such a way that the magnetic fields superimpose with the primary TMS coil field and reduce the induced electric field and current near the affected nerve without reducing the primary magnetic field in the region of therapy. The field produced by such a secondary coil can be lower than that of the primary TMS coil because it is physically placed near the affected nerve and it only needs to serve to diminish the induced current density at the site of nerve stimulation. The secondary coil or coils may also serve to reduce discomfort through other means such as over-stimulating the affected nerve so that it can not respond to further stimulation caused by the TMS field.

FIG. 1 illustrates a ferromagnetic core material magnetic stimulation device 10, or "coil," that may be used in connection with an embodiment of the invention. Device 10 comprises ferromagnetic core 12 surrounded by windings 14. An insulative material 16 is interposed between core 12 and windings 14. Device 10 also includes cable 20 for connecting device 10 to a control system (not shown in FIG. 1 for clarity). Cable 20 may be covered by housing 18 for protection and strain relief.

A ferromagnetic core 12 can be fabricated from various ferromagnetic materials such as, for example, 3% grain oriented silicon steel or vanadium permendur (also known as supermendur). The material is chosen to have, for example, a high saturation level, a sharp-knee B-H curve (i.e., quickly switches from saturated to non-saturated states), low eddy current losses, and a practical cost. The core material may be fabricated into many electrically isolated layers to minimize eddy current losses. The orientation of the lamination may be such as to disrupt the eddy currents (i.e., perpendicular to the direction of induced current flow whenever possible). Also, if the material has a grain orientation, it should be directed parallel to the induced magnetic flux. In one embodiment, the ferromagnetic core is according to U.S. Pat. Nos. 6,132,361 and 5,725,471, each of which is hereby incorporated by reference in their entireties.

In one embodiment, patient treatment typically includes applying a magnetic field to the patient using a coil constructed with an approximately hemispherical ferromagnetic core. The strength of the field and switching rate is sufficient to produce stimulation of the target area in a manner that is appropriate to the type of treatment being administered.

Embodiments of Systems and Methods of Nerve Stimulation

As noted above, transcutaneous stimulation may be used to reduce patient discomfort by directly applying a magnetic field to a problematic nerve such as, for example, a peripheral nerve. In addition, it was also noted above that the transcutaneous stimulation of a patient, while therapeutic, may have undesirable side effects. For example, in the context of transcranial stimulation, cranial nerves, trigeminal nerves, etc., may experience magnetic fields that are above their respective stimulation thresholds. As a result, a patient may experience discomfort from, for example, muscle twitching, pain from sensory nerves, etc. Thus, it is advantageous to target the magnetic field so as to lower the magnetic field at areas that are not to be treated, i.e., at non-treatment area locations.

Thus, discomfort may be reduced in any number of contexts. For example, discomfort may be treated directly, by applying magnetic stimulation to the affected nerve to numb, over-stimulate or otherwise treat the nerve to mitigate the discomfort. It will be appreciated that the magnetic field applied to the nerve may be modified in terms of field strength, pulse repetition rate, vector orientation, frequency characteristics, or the like to achieve a desired effect. Another way to mitigate discomfort is, as noted above, to reduce adverse collateral stimulation that results from magnetic stimulation of tissue in proximity to the treatment area. The methods used to reduce adverse collateral stimulation may be the same or different than the methods used to treat a discomfort-causing nerve. In either context, it can be seen that effective targeting of a therapeutic magnetic field can be used to reduce patient discomfort.

For example, it has been found that some discomfort-causing nerves are more problematic than others. In the context of transcranial magnetic stimulation, for example, it has been found that branches of the trigeminal nerve (located on the left and right sides of the skull) may sometimes be particularly troublesome with respect to unwanted stimulation. Specifically, some branches of the trigeminal nerve are located deeper within the tissue of the skull and penetrate the skull through small openings (foramina) and extend to areas of the face. As described above, the large difference in conductivity between the bone and the nerve penetrating a foramen, the current density is increased at the foramen. Thus, even if superficial cranial nerves are only exposed to sub-stimulation threshold levels of magnetic stimulation, the trigeminal nerve and its branches, though deeper, may be exposed to a higher level of magnetic stimulation that may be above the nerve's stimulation threshold resulting in, for example, facial muscle contractions and/or pain during transcranial magnetic stimulation. Therefore, the magnetic field used to treat a patient should not only be above a stimulation threshold at a treatment location, but should also be locally minimized in sensitive adjacent tissue, such as the trigeminal nerve, to reduce discomfort. Thus, a method for reducing a magnetic field, for example in the region of the trigeminal foramina, to sub-stimulation levels would be advantageous.

Figure 2:
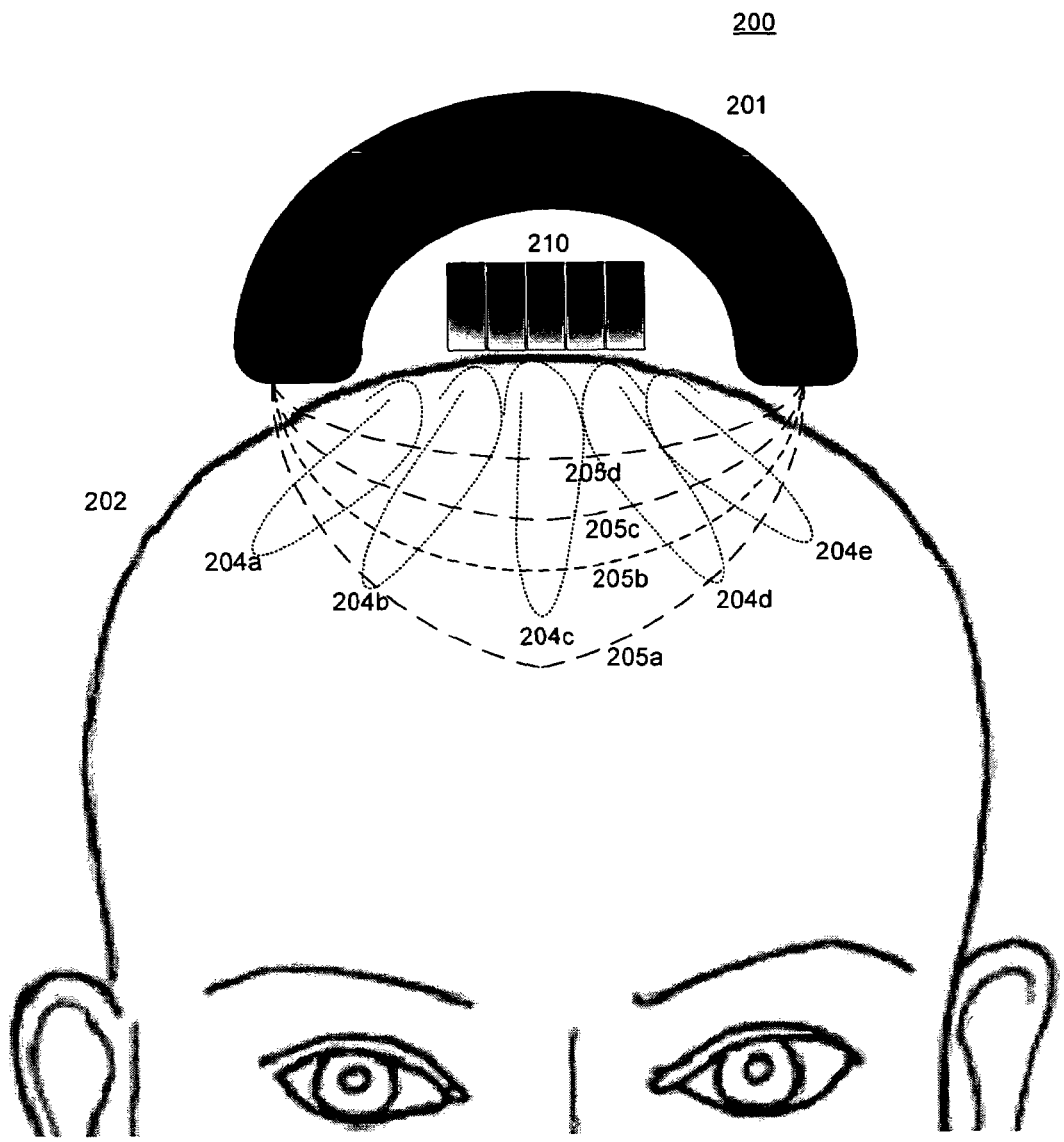
FIG. 2 is a block diagram illustrating a passive technique for reducing discomfort caused by transcutaneous stimulation.

One method that may be employed to target a therapeutic magnetic field may involve the use of a passive component to block or otherwise shape the magnetic field so as to more closely target a treatment area. FIG. 2 is a diagram illustrating a passive technique for reducing discomfort caused by transcutaneous stimulation. As shown in FIG. 2, system 200 includes one or more ferrite pads 210 located above a patient's head 202 and under magnetic stimulation device 201. It should be appreciated that the physical configuration of ferrite pads 210 are illustrated for the purpose of discussion and clarity, and is not meant to be an exclusive representation of such a configuration. For example, ferrite pads 210 may be located between magnetic stimulation device 201 and the patient's head 202. Also, ferrite pads 210 may be attached directly and/or indirectly to the patient's head 202 and/or directly or indirectly connected to magnetic stimulation device 201. In a non-transcranial embodiment, ferrite pads 210 may be placed, for example, between magnetic stimulation device 201 and any location proximate a treatment area. In addition, the number and placement of ferrite pads 210 are not limited to any particular configuration, and may be used in conjunction with any of the other methods described herein.

Ferrite pads 210 operate to effectively "absorb" the magnetic field (lines 204a-e) created by magnetic stimulation device 201. In particular, ferrite pads 210 may be designed and constructed to offset, reduce and/or absorb magnetic field (lines 204a-e) that stimulate the surface-proximate tissue, while permitting magnetic field that penetrates deeper into the patient for therapeutic purposes to pass substantially unaffected. Also, by using a ferrite material, ferrite pads 210 typically have low conductivity and therefore do not encourage induced eddy currents and associated heating or temporal disruption of the therapeutic magnetic field created by magnetic stimulation device 201. It should be appreciated that although system 200 has been described in the context of ferrite material, the pads also may be made of other non-ferrite material and/or a combination of ferrite material and non-ferrite materials.

As can be seen, the ferrite pads 210 are "passive," in that they are not driven by a power source. Rather, the ferrite pads 210 mitigate unwanted stimulation by their mere physical presence. The ferrite pads 210, while effective for mitigating unwanted surface stimulation, are not as effective at mitigating unwanted stimulation at depth because they can only passively absorb the magnetic field (lines 204a-e) created by magnetic stimulation device 210. Furthermore, ferrite pads 210 can only be configured physically (e.g., size, location, shape, etc.), rather than electrically, so the pads 210 are unable to create a magnetic field that can interact, either constructively or destructively, with that of magnetic stimulation device 201.

Figure 3:
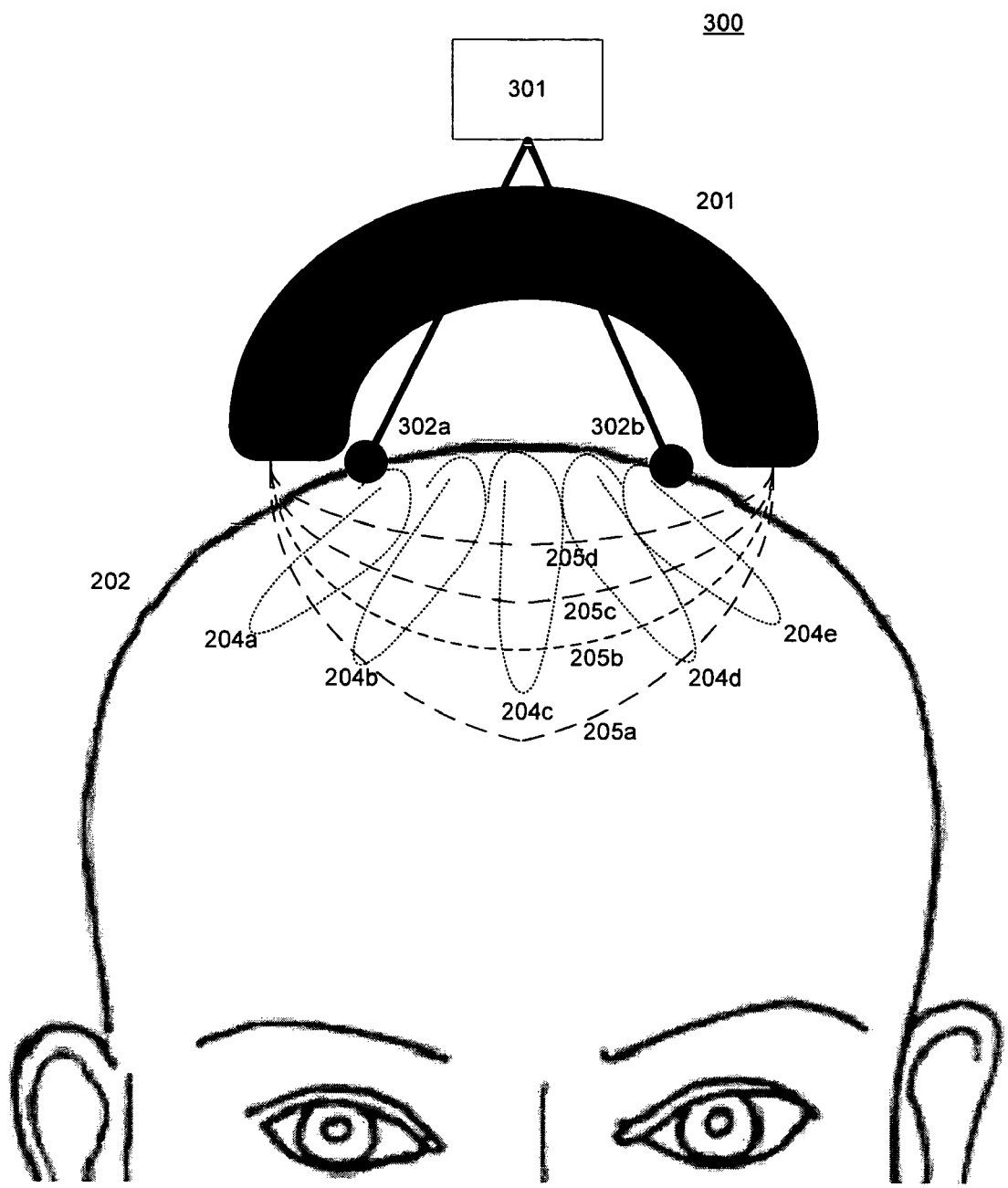
FIG. 3 is a diagram illustrating an active technique for reducing discomfort caused by transcutaneous stimulation.

Therefore, FIG. 3 is a diagram illustrating an active technique for reducing discomfort caused by transcutaneous stimulation. As shown in FIG. 3, system 300 includes power supply 301 in communication with electrodes 302a and 302b. Although two electrodes 302a-b are shown in FIG. 3, it should be appreciated that any number of electrodes may be used.

As previously discussed, magnetic stimulation device 201 creates a pulsed magnetic field (lines 205a-d), which in turn creates an electric field (lines 204a-e). Electric field (204a-e) induces both desirable and undesirable electric currents on and within the patient's head 202. System 300 overcomes the discomfort created by the undesired electric currents at surface-proximate locations, while also permitting the desired electric currents to continue to have their therapeutic effect on the patient at a location deeper within the patient's body. In particular, power supply 301 provides power (i.e., current and/or voltage) to electrodes 302, which conduct the power from power supply 301 to the patient's head 202.

The electrodes may therefore actively reduce discomfort by providing substantially constant or time-varying power to electrodes 302. When the power is substantially constant, the power conducted to the patient's head 202 via electrodes 302 creates a substantially constant electric field in the nerves, muscle and tissues of the patient that lie in between or proximate to electrodes 302. The electric field created by electrodes 302 may have a strength that biases certain cells (i.e., those that are undesirably stimulated by magnetic stimulation device 201). The bias level may be such that the cells are biased near or above their depolarization level. By biasing the cells at or near their depolarization level, electrolytes for example, are redistributed along the cell, thus reducing the ability of the electrolytes to be transported across the cell membrane. Reducing transport of the electrolytes across the cell membrane reduces the possible stimulation of those cells by magnetic stimulation device 201, because the cells may not be as capable of repeatedly responding to the induced electric field created by magnetic stimulation device 201. As a result, the discomfort felt by the patient during treatment is reduced. Although this example was discussed in the context of a substantially constant power source, it should be appreciated that the power need not be applied throughout the entire treatment, but may for example be turned off at any point after the beginning of a pulse corresponding to the therapeutic magnetic stimulation.

Figure 4A:
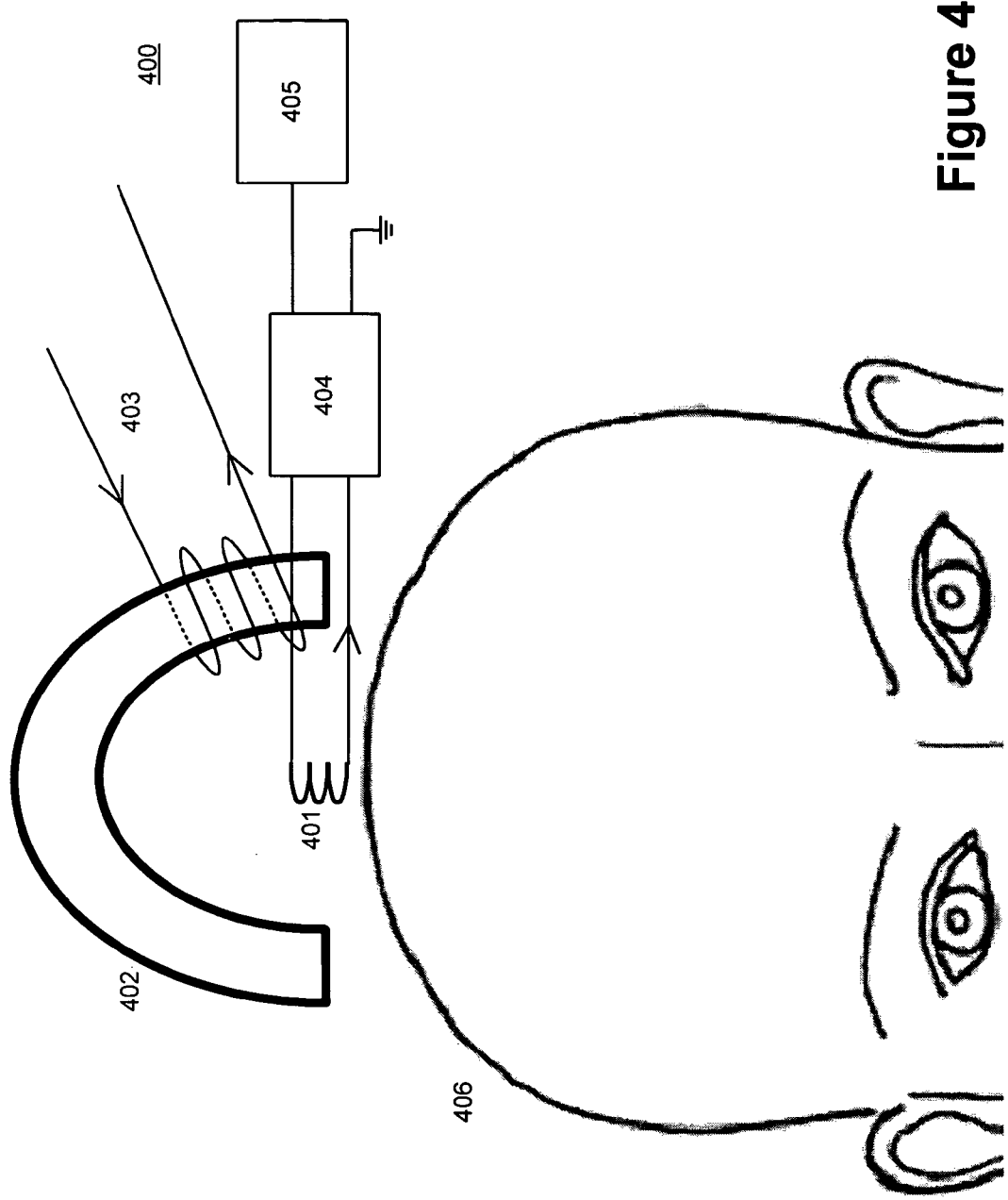
FIG. 4A is a diagram illustrating another active technique for reducing discomfort caused by transcutaneous stimulation.

In addition to, or instead of, a substantially constant power supply provided when the magnetic stimulation is applied, power provided by power source 301 may be time-varying. The time-varying signal from power source 301 may be used to desensitize the muscle, tissue and/or nerves that undesirably are stimulated by magnetic stimulation device 201. In particular, power source 301 may be designed to pre-stimulate (i.e., prior to the therapeutic pulse applied by magnetic stimulation device 201) particular nerves, muscle and/or tissue to reduce their ability to undesirably respond to the otherwise therapeutic pulse. Because electrodes 302 are necessarily placed superficially, this method does not address mitigation of undesired deeper nerve stimulation Turning now to FIG. 4A, a diagram illustrating another active technique for reducing discomfort caused by transcutaneous stimulation is shown. As shown in FIG. 4A, system 400 includes magnetic stimulation device 402 that receives power from stimulation circuit 403 to create magnetic fields (not shown in FIG. 4A for clarity) in the patient's head 406. As previously discussed, magnetic stimulation device 402 creates a pulsed magnetic field that induces current within the patient for certain beneficial therapeutic effects, such as the treatment of depression using TMS, for example. Also, however, the same magnetic field may create discomfort for the patient by undesirably inducing current into surface-proximate tissue, nerves and muscle.

Surface coil 401, located at or near the patient 406 (and possibly between the patient and magnetic stimulation device 402), may be used to offset, eliminate or reduce the undesired effects of the magnetic field created by magnetic stimulation device 402. Pulse programmer 405 generates an appropriate waveform, and drive circuit 404 receive the waveform generated by pulse programmer 405 and provides power to the surface coil 401. Thus, surface coil 401 may generate its own magnetic field that cancels the portion of the magnetic field created by magnetic stimulation device 402 that acts to undesirably stimulate surface-proximate tissue, nerves and muscle. Also, the strength and disposition of the magnetic field created by surface coil 401 may be such that the therapeutic strength of the primary magnetic field created by magnetic stimulation device 402 remains substantially undiminished in the region of therapy.

Figure 4B:
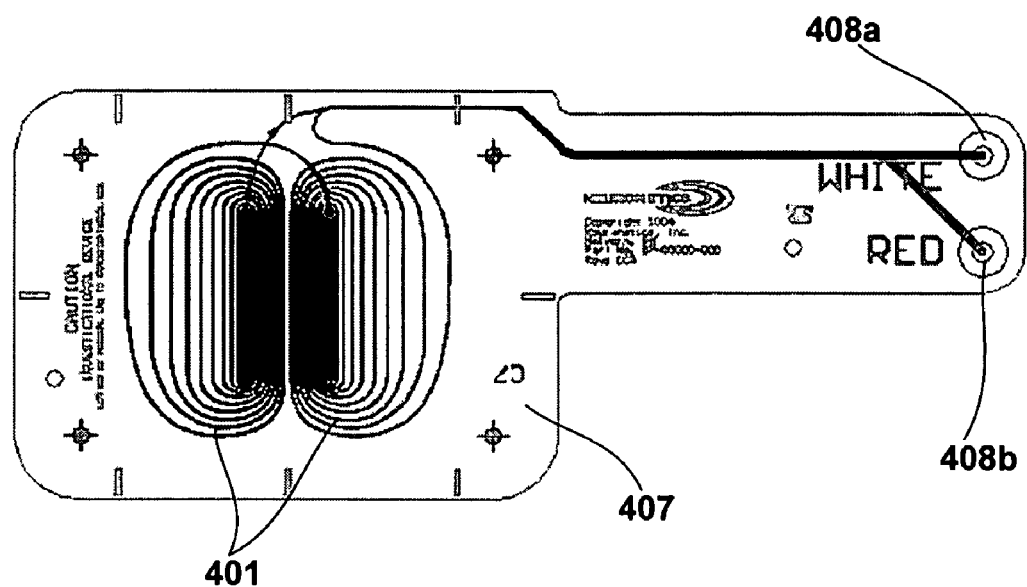
FIG. 4B is a diagram illustrating a coil used to reduce discomfort caused by transcutaneous stimulation.

FIG. 4B is a diagram illustrating a detail view of coil 401 in one embodiment. In such an embodiment, coil 401 is coupled to a mounting pad 407, which may be fabricated from any substance that does not substantially interfere with the operation of coil 401. Mounting pad 407 may, in one embodiment, have an adhesive backing or other fastening means for permitting the mounting pad to be located on a patient's head (e.g., patient 406, not shown in FIG. 4B for clarity). In addition, contacts 408a-b are present to enable coupling of the coil 401 to a power source, such as drive circuit 404 discussed above in connection with FIG. 4A (not shown in FIG. 4B for clarity). As was the case with the techniques discussed above in connection with FIGS. 2-3, the superficial configuration of surface coil 401 limits its ability to mitigate deeper, unwanted stimulation without adversely affecting the magnetic field in the therapeutic region.

As will be discussed below in connection with FIGS. 5-9, an embodiment of the invention provides a plurality of magnetic stimulation devices, or "coils" (e.g., a device having a core such as, for example, a ferromagnetic core material magnetic stimulation device 10 as discussed above in connection with FIG. 1) to enable therapeutic transcutaneous magnetic stimulation while reducing discomfort. An embodiment of the invention uses two or more of such magnetic coils to reduce discomfort without adversely affecting the intended therapy.

For example, and as discussed in detail below in connection with FIGS. 5-9, one embodiment uses a larger first magnetic coil (magnetic stimulation device) to create a relatively unfocused, first magnetic field of sub-stimulation threshold strength throughout an area of a patient in which a treatment area is located (e.g., a patient's head). A smaller, second coil is used to create a relatively focused, second magnetic field of sub-stimulation strength. As discussed above, the magnetic fields may be configured to add (i.e., through superposition) at the treatment area, thereby generating a focused magnetic field that is above a stimulation threshold in the treatment area, thereby enabling therapeutic treatment while minimizing stimulation of the surrounding tissue and reducing discomfort. It will be appreciated that the treatment itself may be directed to reduction of discomfort, in addition to the reduction of discomfort that results from the reduction in stimulation to tissue surrounding the treatment area.

It can be seen that in such an embodiment the larger coil is able to produce a magnetic field that may penetrate deep within a patient, if desired, while the smaller coil produces a focused magnetic field so as to accurately target the treatment area. Thus, the advantages of each size of magnetic coil are exploited, while the shortcomings of each size of coil are mitigated because the large coil is not required to produce a tightly focused magnetic field, and the smaller coil is not required to generate the full strength of a hyperstimulation threshold magnetic field. As will be appreciated, any number, size and/or configuration of coils may be employed in such an embodiment to create a focused magnetic field at one or more treatment areas. Such a configuration may be able to reach treatment locations deep within a patient with a tailored magnetic field to treat discomfort and the like without causing additional or ancillary discomfort in surrounding tissue. Thus, non-treatment areas of the patient can be exposed to even lower magnetic fields than would otherwise be possible with a single magnetic coil.

In another embodiment, and as discussed in detail below in connection with FIGS. 8-9, one or more larger, first magnetic coils may be used to generate a magnetic field that is above a stimulation threshold for a treatment area. One or more smaller, second magnetic coils may be used to generate one or more focused magnetic fields to target a discomfort-causing nerve. As discussed above, the magnetic fields may be configured to cancel each other to the point where the combined magnetic field at the discomfort-causing nerve is below a stimulation threshold, thereby reducing discomfort while not substantially affecting stimulation in the treatment area. Alternatively, the one or more smaller, second magnetic coils may target a discomfort-causing area of stimulation for purposes of intentionally over-stimulating the nerve so the nerve is effectively numbed and cannot respond to the magnetic field. In addition, such an over-stimulation technique may be used at the treatment area itself to reduce discomfort. It will be appreciated that the use of a magnetic coil to perform such cancellation or over-stimulation enables the reduction of discomfort-causing nerve stimulation at locations deep within a patient's body.

While the following discussion describes a two-coil configuration, it will be appreciated that more coils may be used in accordance with an embodiment. In addition, while the following discussion employs a ferromagnetic core magnetic stimulation device, such as the ferromagnetic core material magnetic stimulation device 10 described above in connection with FIG. 1, the use of any type of magnetic stimulation device, including air core coils, is equally consistent with an embodiment of the invention.

Figure 5:
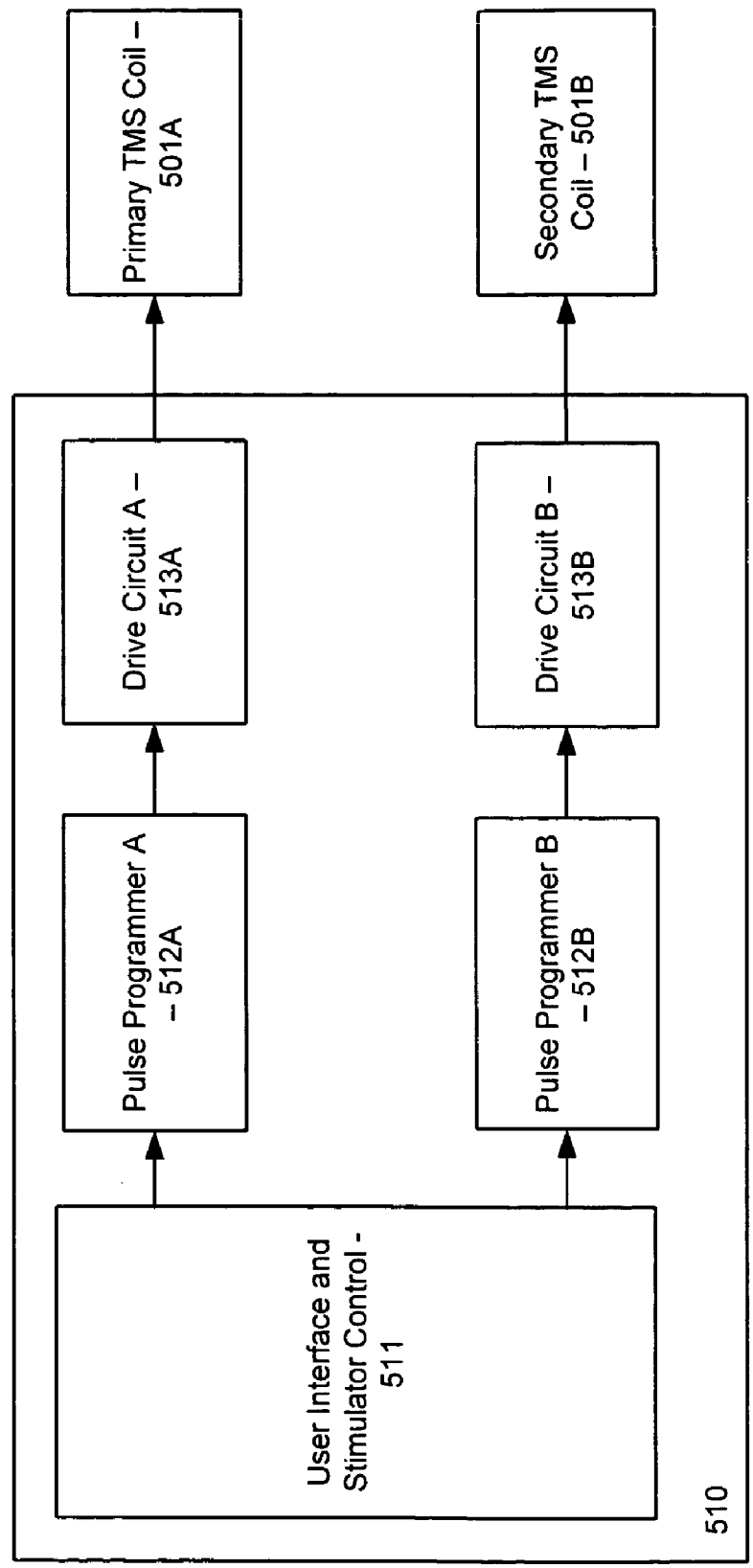
FIG. 5 is a block diagram illustrating a technique for performing transcutaneous stimulation using more than one magnetic stimulation device in accordance with one embodiment of the invention.

FIG. 5 is a block diagram illustrating a technique for performing transcutaneous stimulation using more than one ferromagnetic core coils. Stimulation system 510 controls the operation of the coils by providing a desired amount of power to the coils while pulsing the coils in an appropriate manner. The waveform shape, frequency, etc., may be chosen according to the patient and/or type of treatment being performed. User interface and stimulator control 511 permits a user of stimulation system 510 to enter one or more desired parameters for the operation of the coils. It will be appreciated that any number and/or type of parameters may be entered for purposes of controlling the coils. User interface and stimulator control 511 may be configured in a similar manner to a controller used for the discomfort-reducing techniques discussed above, although it will be appreciated that control 511 may be adapted to control more than one magnetic stimulation coil.

Pulse programmers 512A-B generate the appropriate waveform, according to the parameters received by the user interface and stimulator control 511, for input into each of the drive circuits 513A-B. In one embodiment, additional parameters may automatically be included in the waveform generation process. Drive circuits 513A-B receive the waveforms generated by pulse programmers 512A-B and provide power to the primary and secondary coils 501A-B, respectively.

It will be appreciated that any combination of power and waveform characteristics is equally consistent with an embodiment. For example, primary pulse programmer A 512A may generate a waveform that will result in a magnetic field having different properties than the magnetic field resulting from a waveform generated by secondary pulse programmer B 512B. So long as the magnetic fields have the desired characteristics at the treatment area, any configuration of magnetic fields may be used.

Primary coil 501A generates the primary magnetic field in a manner that was explained above in connection with FIG. 1. As was also noted above, primary coil 501A may provide the main therapeutic magnetic field, or it may be configured to provide a smaller portion of the therapeutic magnetic field. Likewise, secondary coil 501B provides a magnetic field that may be the same as the magnetic field provided by primary coil 501A, or secondary coil 501B may provide a magnetic field having different characteristics from the field generated by primary coil 501A. In addition, each coil 501A-B may be physically identical, or may have different mechanical and/or electromagnetic characteristics.

In one embodiment, primary coil 501A is used to generate a sub-stimulation level magnetic field and secondary coil 501B adds another sub-stimulation level magnetic field to the treatment area. In an embodiment, neither magnetic field alone may be above the stimulation threshold for either the treatment area or for other areas of the patient, such as the cranial nerves, trigeminal nerves, etc. The levels and locations of both sub-stimulation level magnetic fields may be chosen such that the fields add to each other at the desired treatment location, as was discussed above. The combined magnetic field may be of sufficient strength to stimulate the area by depolarizing neurons at the treatment location.

Figure 6A:
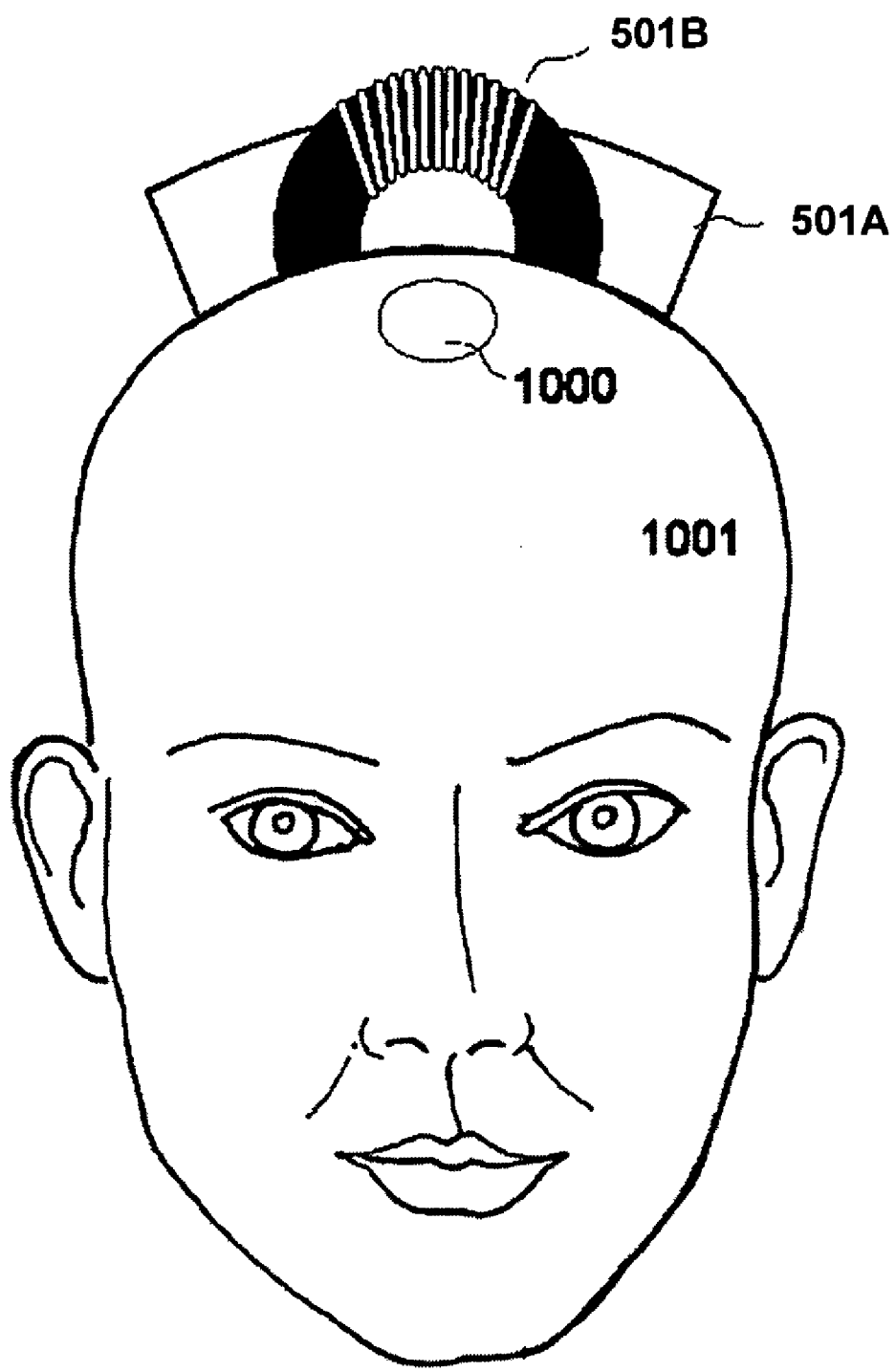
FIGS. 6A-B are diagrams illustrating an exemplary configuration of multiple magnetic stimulation devices used to perform transcutaneous stimulation in accordance with one embodiment of the invention.
Figure 6B:
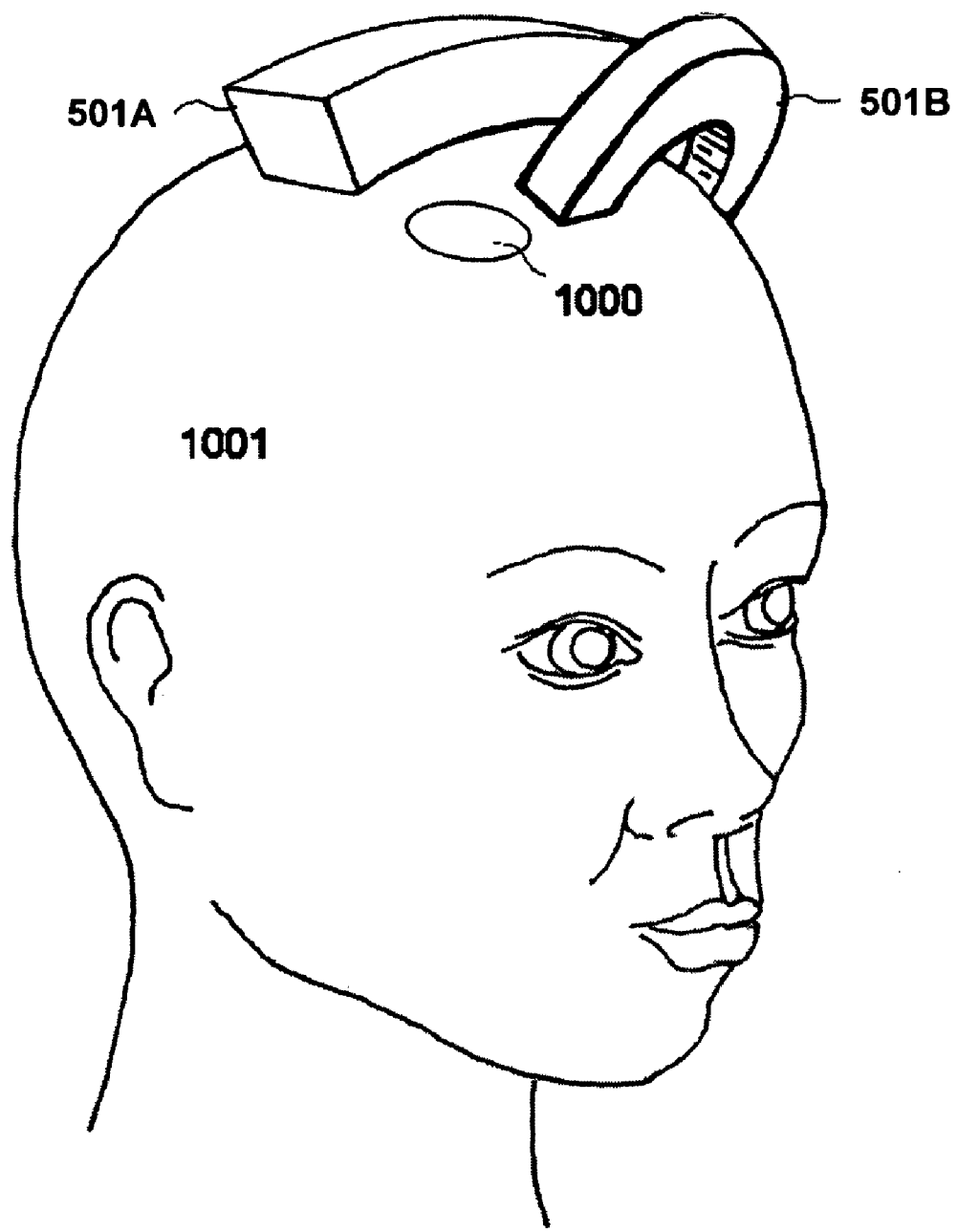

FIGS. 6A and 6B are diagrams illustrating an exemplary configuration of multiple magnetic stimulation devices (e.g., multiple ferromagnetic core magnetic stimulation devices) used to perform transcutaneous stimulation. It can be seen that FIG. 6A is a frontal view of a patient 1001, while FIG. 6B is a perspective view of patient 1001. Primary coil 501A and secondary coil 501B are as described above in connection with FIG. 5. A patient's head 1001 is shown, and treatment area 1000 is illustrated at an arbitrary location within the patient's head 1001. It will be appreciated that the configuration of FIG. 6A may be adapted to provide a therapeutic magnetic field to a treatment area that is at any location on the patient, and is not limited to patient's head 1001.

In FIGS. 6A-B, primary coil 501A may be the "main" coil that provides the majority of the therapeutic magnetic field, while secondary coil 501B may provide a localized magnetic field to create a magnetic field at treatment area 1000 that is above a stimulation threshold. For example, primary coil 501A may produce a sub-stimulation level magnetic field for all points within the skull. The smaller, secondary coil 501B may be pulsed in synchrony with the primary coil to produce a magnetic field that is localized so as to target the treatment area 1001. The sum of the fields from coils 501A and B may be above the stimulation threshold in treatment area 1000 and may rapidly fall off to sub-stimulation levels outside the target region, thus exposing cranial nerves, and particularly trigeminal nerves, to a sub-stimulation level magnetic field. It will be appreciated that the coils 501A and B may be designed so that the magnetic field at the trigeminal nerve (particularly at the foramina) is sufficiently reduced so no sensation is felt by patient 1001, for example. It will be appreciated that while treating other nerves in other locations within a body, the coil configuration discussed above may be able to treat patient discomfort in peripheral nerves even when such nerves are deep within the patient's body.

Figure 7:
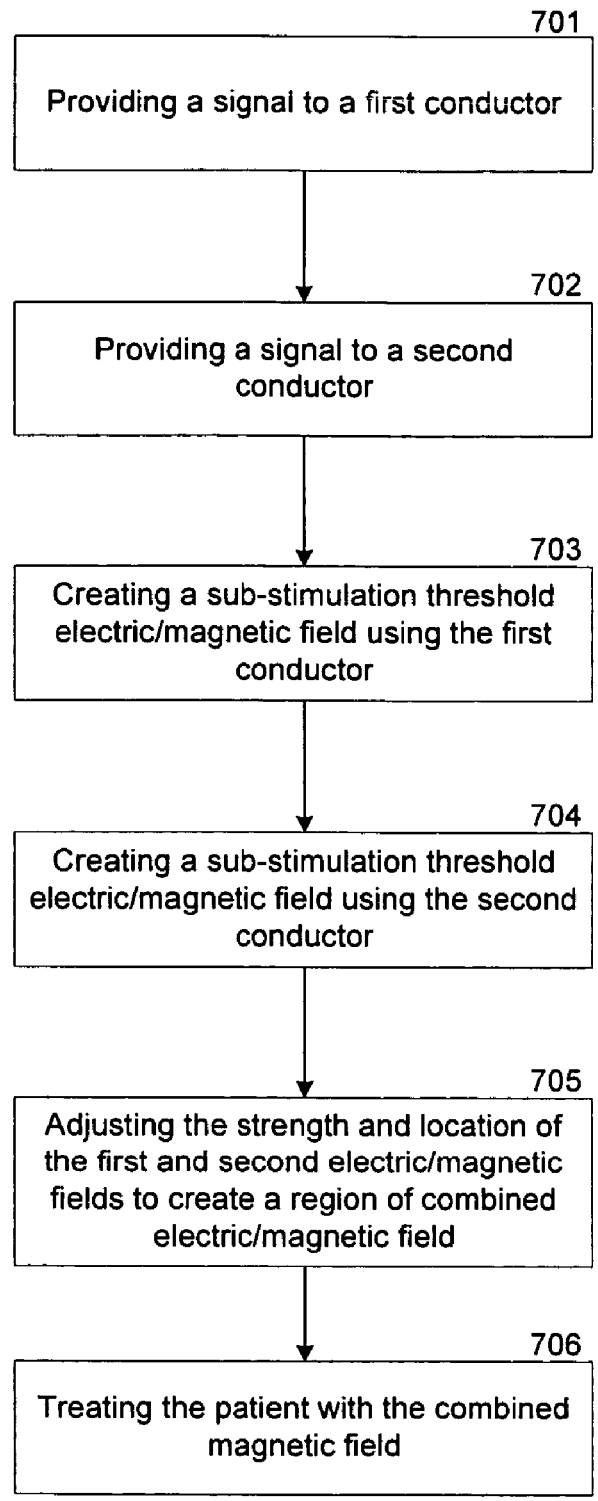
FIG. 7 is a flowchart illustrating the use of multiple magnetic stimulation devices to perform transcutaneous stimulation in accordance with one embodiment of the invention.

FIG. 7 is a flowchart illustrating the use of multiple magnetic stimulation devices to perform transcutaneous stimulation. The illustrated method 700 facilitates transcutaneous magnetic stimulation treatments while minimizing patient discomfort. At step 701, a signal may be provided to a first conductor. It will be appreciated that, in an embodiment, the signal may be generated by primary drive circuit 513A described above in connection with FIG. 5, and is sent to the first conductor, which may be part of primary coil 501A. Likewise, at step 702, a signal is provided to a second conductor. It will be appreciated that, in an embodiment, the signal is generated by secondary drive circuit 513B and may be sent to the second conductor, which is part of secondary coil 501B.

At step 703, a sub-stimulation threshold electric and/or magnetic field is created using the first conductor. For example, in an embodiment, primary coil 501A is pulsed to create a magnetic field as was described above in connection with FIGS. 6A-B. It may be appreciated that this magnetic field may be a relatively unfocused field, as was also discussed above. At step 704, another sub-stimulation threshold electric and/or magnetic field may be created using the second conductor. Again, it may be appreciated that this field may be a relatively focused field as was also discussed above. For example, secondary coil 501B may be pulsed to create a magnetic field as was also described above in connection with FIGS. 6A-B. At step 705, the strength and location, and possibly other parameters, of the magnetic fields generated by the conductors are adjusted to create a region of combined electric and/or magnetic field. It will be appreciated that adjustments might not be necessary in step 705 if the electric and/or magnetic fields were correctly configured initially.

At step 706, the patient is treated with the combined magnetic field in connection with transcutaneous magnetic stimulation treatment such as, for example, TMS, rTMS or the like. It will be appreciated that by performing such stimulation and treatment in the manner described in FIG. 7 the patient is able to receive treatment with a minimum of discomfort.

As noted above, a plurality of coils may be configured in any number of ways while still remaining consistent with an embodiment of the invention. For example, a configuration in accordance with one embodiment uses a first coil (e.g., the primary coil 501A) in a conventional TMS fashion, where the first coil provides sufficient field strength for the desired TMS stimulation. In addition, however, a second coil (e.g., the secondary coil 501B) may be used to mitigate cranial nerve discomfort by placing the second coil proximate the discomfort-causing cranial nerve.

By using two coils in such a manner, and as discussed above, an embodiment may be configured to either cause the second coil to cancel some or all of the magnetic field in the region of the cranial nerve that is causing the patient discomfort (referred to as "localized field cancellation"), or the second coil may be used to intentionally over-stimulate the cranial nerve so the nerve is numbed and is therefore unable to respond to the pulses from the first coil (referred to as "over-stimulation"). Localized field cancellation using the second coil may be very important in certain applications where sensation from the first coil is particularly acute. One such application is, for example, the use of TMS for treatment of schizophrenia (i.e., auditory hallucinations). In this application, the target region is near superficial musculature and trigeminal nerve branches. In an embodiment, the second coil may be empirically placed to minimize sensations during such a procedure. It will be appreciated that the orientation of the second coil with respect to the first coil in this particular embodiment should cause the fields to cancel.

Over-stimulation of one or more problematic nerves is another variation of this embodiment. In such an application, the second coil is operated with a pulse waveform whose frequency is optimized to couple with the cranial nerve. It is repeatedly pulsed at a rate sufficient to guarantee that the nerve cannot repolarize and respond to external stimulus. Pulsing of the second coil is not necessarily synchronized with the primary TMS treatment. In an embodiment the two coils may be oriented so their fields do not add in the event that both coils were to be pulsed simultaneously. Alternatively, the second coil may be sequenced such that it will not be pulsed when a primary TMS treatment pulse is applied.

Figure 8:
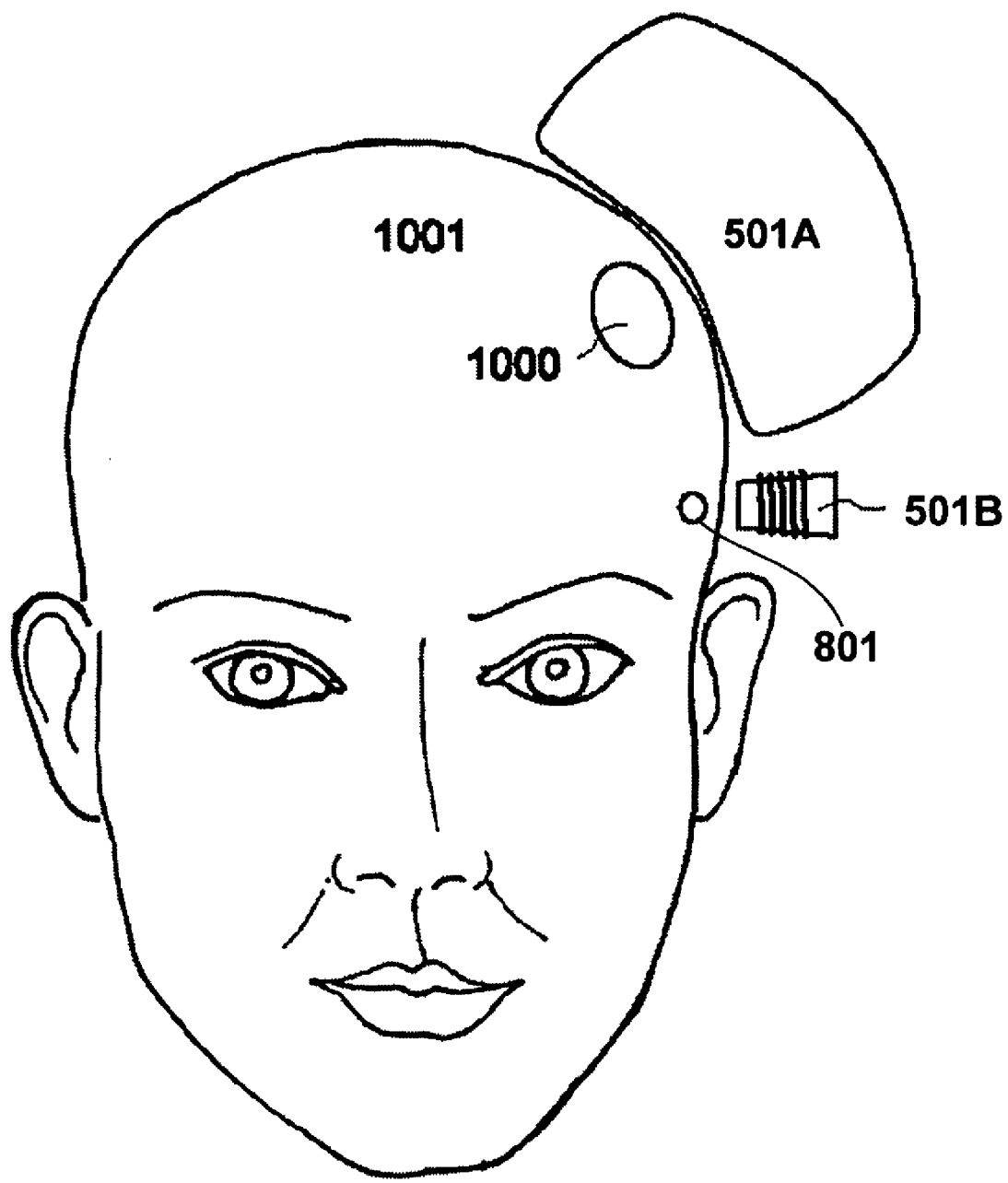
FIG. 8 is a diagram illustrating an exemplary configuration of multiple magnetic stimulation devices used to reduce discomfort caused by transcutaneous stimulation in accordance with one embodiment of the invention.

Accordingly, FIG. 8 is a block diagram illustrating an exemplary configuration of multiple magnetic stimulation devices used to reduce discomfort caused by transcutaneous stimulation. It will be appreciated that the configuration of FIG. 8 may be used in either context described above; that is, either for localized field cancellation and/or for over-stimulation. In addition, the configuration of FIG. 8 is described in connection with transcranial treatment for purposes of explanation and clarity, as the configuration may be used in connection with any treatment method, including the methods listed above. Thus, primary coil 501A provides a primary, therapeutic magnetic field that is sufficient for the desired stimulation at treatment area 1000 within a patient's head 1001. Secondary coil 501B provides a second magnetic field that is directed to cranial nerve 801. It will be appreciated that cranial nerve 801 can be any type of cranial nerve or nerves in any region of patient's head 1001 that is causing as a result of the stimulation treatment. The magnetic field provided by secondary coil 501B, depending on the field characteristics, may either provide for localized field cancellation by canceling a part of the primary magnetic field, or for over-stimulation by ensuring that cranial nerve 801 cannot repolarize during the transcranial magnetic stimulation procedure.

Figure 9:
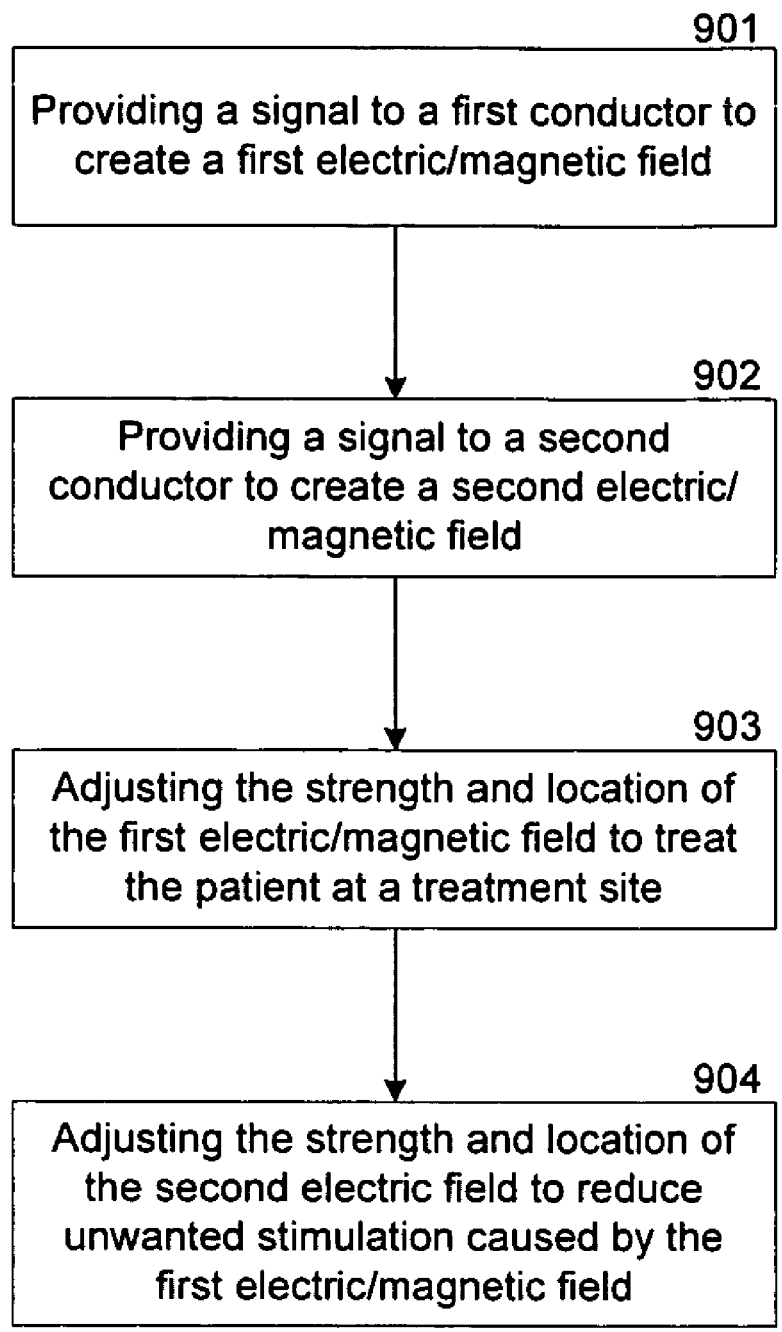
FIG. 9 is a flowchart illustrating the use of multiple magnetic stimulation devices to reduce discomfort caused by transcutaneous stimulation in accordance with one embodiment of the invention.

FIG. 9 is a flowchart illustrating the use of multiple magnetic stimulation devices to reduce discomfort caused by transcutaneous stimulation. The method 900 illustrated in FIG. 9 applies equally to localized field cancellation and to over-stimulation for reducing discomfort during any type of transcranial magnetic stimulation such as, for example, TMS, rTMS or other treatments. At step 901, a signal is provided to a first conductor (e.g., primary coil 501A) to create a primary electric and/or magnetic field that may be both above the stimulation threshold and sufficient for treatment purposes at the treatment area. For example, in an embodiment primary coil 501A is pulsed to create a magnetic field as was described above in connection with FIG. 11.

At step 902, a signal is provided to a second conductor (e.g., secondary coil 501B) to create a secondary electric and/or magnetic field. For example, in an embodiment, secondary coil 501A is pulsed to create a magnetic field as was described above in connection with FIG. 11. At step 903, the strength and location, and possibly other parameters, of the magnetic field generated by the first conductor is adjusted to provide a therapeutic magnetic field at the treatment area. As will be appreciated, the method 900, the first conductor generates the full, therapeutic magnetic field on its own. It will also be appreciated that adjustments might not be necessary in step 903 if the electric and/or magnetic fields were correctly configured initially.

At step 904, the strength and location, and possibly other parameters, of the magnetic field generated by the second conductor are adjusted. In one embodiment, the second conductor may provide a localized magnetic field that will sufficiently cancel the magnetic field created by the first conductor at a region associated with a discomfort-causing nerve or other tissue the stimulation of which causes patient discomfort or is otherwise undesired. In such a manner, the magnetic field experienced by the nerve is below its stimulation threshold. In another embodiment, the second conductor provides a magnetic field that over-stimulates the discomfort-causing nerve so as to prevent the nerve from repolarizing during the treatment.

It will be appreciated that method 900 and method 700 of FIG. 7 may be combined. For example, a therapeutic magnetic field may be created by more than one primary coil according to method 700 of FIG. 7. In addition, one or more other coils may be operated according to method 900 to reduce discomfort caused by the magnetic fields created by the primary coils. The methods of reducing discomfort may therefore be combined in any number of configurations.

It will also be appreciated that unmyelinated neurons (i.e., neurons that are not covered by a myelin sheath, such as cortical neurons) have a different frequency response characteristic than myelinated neurons (i.e., different chronaxies or response time constants). This fact advantageously can be leveraged by optimizing the pulse frequency for the intended neuron. For example, the second coil may be "tuned" for the myelinated cranial nerve and may therefore be less effective in stimulating cortical neurons. Likewise, the first coil may operate at a pulse frequency that best stimulates unmyelinated neurons, thereby minimizing unwanted stimulation of cranial nerves. It will be appreciated that such "tuning" may be employed in connection with any technique, or combination of techniques, described herein.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed:

1. A method for performing transcutaneous magnetic stimulation, comprising:
    creating a first magnetic field at a first and second location using a first magnetic stimulation device, wherein the first magnetic field causes magnetic stimulation at the first and second locations; and
    adjusting a placement of a second magnetic stimulation device with respect to the first magnetic stimulation device to create a second magnetic field at the second location that destructively interferes with the first magnetic field at the second location, wherein the magnetic stimulation at the first location is sufficient for the transcutaneous magnetic stimulation.

2. The method of claim 1, wherein the magnetic stimulation at the second location is reduced by reducing a magnetic field flux density at the second location.

3. The method of claim 1, wherein the first location is a treatment area.

4. The method of claim 1, wherein the second location is a treatment area.

5. The method of claim 1, wherein the first location is a brain.

6. The method of claim 5, wherein the second location is a cranial nerve.

7. The method of claim 5, wherein the second location is a trigeminal nerve.

8. The method of claim 1, wherein the second location is a location that is sensitive to pain.

9. The method of claim 1, wherein reducing the stimulation at the second location comprises over-stimulating the second location with the second magnetic field.

10. The method of claim 9, wherein the over-stimulation reduces the second location's sensitivity to pain.

11. The method of claim 10, wherein the over-stimulation reduces the second location's ability to respond to the magnetic stimulation.

12. The method of claim 11, wherein the over-stimulation prevents the second location from repolarizing.

13. The method of claim 1, further comprising detecting the first magnetic field, and wherein the second magnetic field is created based on the detected first magnetic field.

14. The method of claim 1, wherein the magnetic stimulation is canceled with a magnetic field.

15. The method of claim 1, wherein the method is used for the treatment of depression or schizophrenia.

16. A system for performing transcutaneous magnetic stimulation, comprising:
    a first magnetic stimulation device for creating a first magnetic field for transcutaneously stimulating a first and second location; and
    a second magnetic stimulation device adapted for adjusting the placement of the second magnetic stimulation device with respect to the first magnetic stimulation device to create a second magnetic field for destructively interfering with the first magnetic field at the second location, wherein the magnetic stimulation at the first location is sufficient for the transcutaneous magnetic stimulation.

17. The system of claim 16, further comprising a stimulator circuit in communication with the first and second magnetic stimulation devices.

18. The system of claim 17, wherein the stimulator circuit provides a first signal to the first magnetic stimulation device and a second signal to a second magnetic stimulation device.

19. The system of claim 18, wherein the first and second signals are different.

20. The system of claim 16, wherein the first and second magnetic stimulation devices are oriented as a function of their magnetic fields.

21. The system of claim 16, wherein the first and second magnetic stimulation devices have a different characteristic.

22. The system of claim 21, wherein the different characteristic is a different shape.

23. The system of claim 21, wherein the different characteristic is a different size.

24. The system of claim 23, wherein the first magnetic stimulation device is larger than the second magnetic stimulation device.

25. The system of claim 16, wherein the first and second magnetic stimulation devices have a ferromagnetic core.

26. The system of claim 25, wherein the first magnetic stimulation device has flat wire windings disposed around its ferromagnetic core.

27. The system of claim 25, wherein the second magnetic stimulation device has flat wire windings disposed around its ferromagnetic core.

28. The system of claim 16, wherein the first magnetic stimulation device is adapted to be placed on a head.

29. The system of claim 16, wherein the first magnetic stimulation device is placed proximate a peripheral nerve.

30. The system of claim 16, wherein power is provided to the first and second magnetic stimulation devices at a substantially similar time for a substantially similar duration.

31. The system of claim 30, wherein the power is pulsed to the first and second magnetic stimulation devices at substantially the same time.

32. The system of claim 30, wherein the power is pulsed to the first and second magnetic stimulation devices at a substantially different time.

* * * * *